(12) United States Patent
Sharma et al.

(10) Patent No.: US 11,052,243 B2
(45) Date of Patent: Jul. 6, 2021

(54) LAPAROSCOPIC LEAD FOR ESOPHAGEAL SPHINCTER IMPLANTATION

(71) Applicant: EndoStim, Inc., Dallas, TX (US)

(72) Inventors: Virender K. Sharma, Paradise Valley, AZ (US); Shai Policker, Tenafly, NJ (US); Paul V. Goode, Round Rock, TX (US); Ofer Glasberg, Zichron Ya'akov (IL)

(73) Assignee: ENDOSTIM (ABC), LLC, San Ramon, CA (US)

( * ) Notice: Subject to any disclaimer, the term of this patent is extended or adjusted under 35 U.S.C. 154(b) by 0 days.

(21) Appl. No.: 15/891,209

(22) Filed: Feb. 7, 2018

(65) Prior Publication Data

US 2019/0054291 A1 Feb. 21, 2019

Related U.S. Application Data

(60) Division of application No. 14/548,855, filed on Nov. 20, 2014, now Pat. No. 9,925,367, which is a (Continued)

(51) Int. Cl.
*A61N 1/05* (2006.01)
*A61B 17/04* (2006.01)
(Continued)

(52) U.S. Cl.
CPC ........ *A61N 1/0509* (2013.01); *A61B 17/0401* (2013.01); *A61N 1/0517* (2013.01);
(Continued)

(58) Field of Classification Search
CPC .. A61N 1/0509; A61N 1/0517; A61N 1/0558; A61N 1/0592; A61N 2001/0582;
(Continued)

(56) References Cited

U.S. PATENT DOCUMENTS 3,909,883 A   10/1975   Fegen
3,910,281 A   10/1975   Kletschka
(Continued)

FOREIGN PATENT DOCUMENTS

CN   1476339   2/2004
CN   1494451 A   5/2004
(Continued)

OTHER PUBLICATIONS

Office Action dated May 20, 2016 for U.S. Appl. No. 13/975,162.
(Continued)

*Primary Examiner* — Paula J Stice
(74) *Attorney, Agent, or Firm* — Novel IP

(57) ABSTRACT

A method of laparoscopically implanting an electrically stimulating lead proximate the lower esophageal sphincter (LES) of a patient includes delivering the lead through a port of a laparoscope inserted into the abdominal cavity of the patient through an incision in the abdominal wall. The stimulating electrode is implanted in or proximate the muscularis layer of the lower esophageal wall to treat esophageal reflux disease (GERD). The lead includes a needle and suture at its distal end for pulling the electrode into the muscular wall of the LES. Clips are applied to the suture attached to the distal end of the lead to prevent retrograde movement of the electrode. The lead also includes an anchoring member for anchoring the portion of the lead proximal to the electrode. The method and lead used with the method allow the surgeon to work within the confined anatomy present at the gastroesophageal junction and prevents backwards movement and dislodgment of the electrode. The implantation procedure can be combined with a hiatal hernia repair to repair the hernia and prevent recurrence of a hiatal hernia.

14 Claims, 7 Drawing Sheets

Related U.S. Application Data continuation-in-part of application No. 13/602,184, filed on Sep. 2, 2012, now Pat. No. 9,037,245.

(60) Provisional application No. 61/906,825, filed on Nov. 20, 2013, provisional application No. 61/530,781, filed on Sep. 2, 2011.

(51) Int. Cl.
*A61B 1/313* (2006.01)
*A61B 17/00* (2006.01)

(52) U.S. Cl.
CPC ... *A61B 1/3132* (2013.01); *A61B 2017/00818* (2013.01); *A61B 2017/00827* (2013.01); *A61B 2017/0417* (2013.01)

(58) Field of Classification Search
CPC .............. A61B 17/0407; A61B 1/3132; A61B 2017/00818; A61B 2017/00827; A61B 2017/0417
See application file for complete search history.

(56) References Cited

U.S. PATENT DOCUMENTS

| | | |
|---|---|---|
| 4,393,883 A | 7/1983 | Smyth |
| 4,414,986 A | 11/1983 | Dickhudt |
| 4,612,934 A | 9/1986 | Borkan |
| 4,735,205 A | 4/1988 | Chachques |
| 5,117,827 A | 6/1992 | Stuebe |
| 5,188,104 A | 2/1993 | Wernicke |
| 5,193,539 A | 3/1993 | Schulman |
| 5,197,491 A | 3/1993 | Anderson |
| 5,231,988 A | 8/1993 | Wernicke |
| 5,263,480 A | 11/1993 | Wernicke |
| 5,292,344 A | 3/1994 | Douglas |
| 5,360,428 A | 11/1994 | Hutchinson, Jr. |
| 5,423,872 A | 6/1995 | Cigaina |
| 5,531,778 A | 7/1996 | Maschino |
| 5,540,730 A | 7/1996 | Terry, Jr. |
| 5,556,425 A | 9/1996 | Hewson |
| 5,606,242 A | 2/1997 | Hull |
| 5,633,573 A | 5/1997 | van Phuoc |
| 5,649,902 A | 7/1997 | Yoon |
| 5,674,205 A | 10/1997 | Pasricha |
| 5,690,691 A | 11/1997 | Chen |
| 5,697,375 A | 12/1997 | Hickey |
| 5,709,224 A | 1/1998 | Behl |
| 5,716,385 A | 2/1998 | Mittal |
| 5,716,392 A | 2/1998 | Bourgeois |
| 5,769,881 A | 6/1998 | Schroeppel |
| 5,810,810 A | 9/1998 | Tay |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,893,883 A | 4/1999 | Torgerson |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,221,039 B1 | 4/2001 | Durgin |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,360,130 B1 | 3/2002 | Duysens |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,611,715 B1 | 8/2003 | Boveja |
| 6,612,983 B1 | 9/2003 | Marchal |
| 6,615,084 B1 | 9/2003 | Cigaina |
| 6,678,561 B2 | 1/2004 | Forsell |
| 6,684,104 B2 | 1/2004 | Gordon |
| 6,749,607 B2 | 6/2004 | Edwards |
| 6,754,536 B2 | 6/2004 | Swoyer |
| 6,760,626 B1 | 7/2004 | Boveja |
| 6,820,019 B1 | 11/2004 | Kelly |
| 6,826,428 B1 | 11/2004 | Chen |
| 6,832,114 B1 | 12/2004 | Whitehurst |
| 6,853,862 B1 | 2/2005 | Marchal |
| 6,876,885 B2 | 4/2005 | Swoyer |
| 6,879,859 B1 | 4/2005 | Boveja |
| 6,879,861 B2 | 4/2005 | Benz |
| 6,901,295 B2 | 5/2005 | Sharma |
| 6,915,165 B2 | 7/2005 | Forsell |
| 6,947,792 B2 | 9/2005 | Ben-Haim |
| 6,952,613 B2 | 10/2005 | Swoyer |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | DiLorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,395 B2 | 4/2010 | Towe |
| 7,702,934 B2 | 4/2010 | Imran |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,809,442 B2 | 10/2010 | Bolea |
| 7,813,809 B2 | 10/2010 | Strother |
| 7,835,796 B2 | 11/2010 | Maschino |
| 7,848,802 B2 | 12/2010 | Goetz |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 | 4/2012 | Soffer |
| 8,185,206 B2 | 5/2012 | Starkebaum |
| 8,282,561 B2 | 10/2012 | Towe |
| 8,380,321 B2 | 2/2013 | Goetz |

(56) References Cited

U.S. PATENT DOCUMENTS

| | | |
|---|---|---|
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |
| 8,718,771 B2 | 5/2014 | Gandhi |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,037,245 B2 | 5/2015 | Sharma |
| 9,061,147 B2 | 5/2015 | Sharma |
| 9,498,619 B2 | 11/2016 | Goode |
| 2001/0041831 A1 | 11/2001 | Starkweather |
| 2002/0103522 A1 | 8/2002 | Swoyer |
| 2002/0138075 A1 | 9/2002 | Edwards |
| 2002/0161414 A1 | 10/2002 | Flesler |
| 2002/0165589 A1 | 11/2002 | Imran |
| 2003/0014086 A1 | 1/2003 | Sharma |
| 2003/0028226 A1 | 2/2003 | Thompson |
| 2003/0055463 A1 | 3/2003 | Gordon |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0010290 A1 | 1/2004 | Schroeppel |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | Parks |
| 2006/0015162 A1 | 1/2006 | Edward |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | Dilorenzo |
| 2006/0149337 A1 | 7/2006 | John |
| 2006/0167498 A1 | 7/2006 | DiLorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247722 A1 | 11/2006 | Maschino |
| 2006/0265021 A1 | 11/2006 | Herbert |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0114971 A1 | 5/2007 | Uesaka |
| 2007/0142699 A1 | 6/2007 | Jandrall |
| 2007/0142831 A1 | 6/2007 | Shadduck |
| 2007/0142884 A1 | 6/2007 | Jandrall |
| 2007/0156182 A1 | 7/2007 | Castel |
| 2007/0162084 A1 | 7/2007 | Chen |
| 2007/0162085 A1 | 7/2007 | Dilorenzo |
| 2007/0179542 A1 | 8/2007 | Prakash |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2007/0293910 A1 | 12/2007 | Strother |
| 2008/0021512 A1 | 1/2008 | Knudson |
| 2008/0039904 A1 | 2/2008 | Bulkes |
| 2008/0046062 A1 | 2/2008 | Camps |
| 2008/0058836 A1 | 3/2008 | Moll |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0076498 A1 | 3/2009 | Saadat |
| 2009/0088817 A1 | 4/2009 | Starkebaum |
| 2009/0131993 A1 | 5/2009 | Rousso |
| 2009/0132001 A1 | 5/2009 | Soffer |
| 2009/0187223 A1 | 7/2009 | Gross |
| 2009/0192564 A1 | 7/2009 | Armstrong |
| 2009/0204063 A1 | 8/2009 | Policker |
| 2009/0264951 A1 | 10/2009 | Sharma |
| 2009/0281553 A1 | 11/2009 | Kalloo |
| 2010/0004648 A1 | 1/2010 | Edwards |
| 2010/0010388 A1 | 1/2010 | Panken |
| 2010/0049026 A1 | 2/2010 | Gerber |
| 2010/0057085 A1 | 3/2010 | Holcomb |
| 2010/0069789 A1 | 3/2010 | Hirota |
| 2010/0076345 A1 | 3/2010 | Soffer |
| 2010/0170812 A1 | 7/2010 | Odierno |

(56) References Cited

U.S. PATENT DOCUMENTS

| | | | |
|---|---|---|---|
| 2010/0198039 | A1 | 8/2010 | Towe |
| 2010/0268495 | A1 | 10/2010 | Armstrong |
| 2010/0324432 | A1 | 12/2010 | Bjoerling |
| 2011/0004266 | A1 | 1/2011 | Sharma |
| 2011/0034967 | A1 | 2/2011 | Chen |
| 2011/0046653 | A1 | 2/2011 | Addington |
| 2011/0071589 | A1 | 3/2011 | Starkebaum |
| 2011/0213437 | A9 | 9/2011 | Armstrong |
| 2011/0224665 | A1 | 9/2011 | Crosby |
| 2011/0295335 | A1 | 12/2011 | Sharma |
| 2011/0295336 | A1 | 12/2011 | Sharma |
| 2011/0307027 | A1 | 12/2011 | Sharma |
| 2011/0307028 | A1 | 12/2011 | Sharma |
| 2012/0232610 | A1 | 9/2012 | Soffer |
| 2012/0259389 | A1 | 10/2012 | Starkebaum |
| 2012/0265103 | A1 | 10/2012 | Policker |
| 2012/0277619 | A1 | 11/2012 | Starkebaum |
| 2013/0030503 | A1 | 1/2013 | Yaniv |
| 2013/0035740 | A1 | 2/2013 | Sharma |
| 2013/0072928 | A1 | 3/2013 | Schaer |
| 2013/0090551 | A1 | 4/2013 | Sharma |
| 2013/0178912 | A1 | 7/2013 | Sharma |
| 2013/0218229 | A1 | 8/2013 | Sharma |
| 2013/0231660 | A1 | 9/2013 | Edwards |
| 2013/0238048 | A1 | 9/2013 | Almendinger |
| 2014/0012348 | A1 | 1/2014 | Starkebaum |
| 2014/0018657 | A1 | 1/2014 | Sharma |
| 2014/0088664 | A1 | 3/2014 | Sharma |
| 2014/0088666 | A1 | 3/2014 | Goetz |
| 2014/0135886 | A1 | 5/2014 | Cook |
| 2014/0222106 | A1 | 8/2014 | Sharma |
| 2014/0228911 | A1 | 8/2014 | Sharma |
| 2014/0243593 | A1 | 8/2014 | Goode |
| 2015/0045786 | A1 | 2/2015 | Edwards |
| 2015/0119952 | A1 | 4/2015 | Sharma |
| 2016/0001071 | A1 | 1/2016 | Sharma |

FOREIGN PATENT DOCUMENTS

| | | |
|---|---|---|
| CN | 102725021 | 10/2012 |
| EP | 1004330 | 5/2000 |
| WO | 199853878 | 12/1998 |
| WO | 9903532 | 1/1999 |
| WO | 9930776 | 6/1999 |
| WO | 0061223 A1 | 10/2000 |
| WO | 0061224 A1 | 10/2000 |
| WO | 2000061223 | 10/2000 |
| WO | 2000061224 | 10/2000 |
| WO | 0243467 A2 | 6/2002 |
| WO | 2002043467 | 6/2002 |
| WO | 02089655 | 11/2002 |
| WO | 2005051486 A1 | 9/2005 |
| WO | 2007137026 | 11/2007 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

Office Action dated May 4, 2016 for U.S. Appl. No. 14/548,793.
Office Action dated Jun. 8, 2016 for U.S. Appl. No. 14/475,736.
Notice of Allowance dated Jul. 19, 2016 for U.S. Appl. No. 14/191,085.
Supplementary European Search Report for EP13831668, completed on Apr. 15, 2016.
Office Action dated Aug. 24, 2016 for U.S. Appl. No. 14/753,402.
Office Action dated Aug. 19, 2016 for U.S. Appl. No. 14/943,772.
Notice of Allowance dated Sep. 27, 2016 for U.S. Appl. No. 14/500,856.
Office Action dated Oct. 3, 2016 for U.S. Appl. No. 14/548,793.
Second Office Action for Chines Patent Application No. 201380054290.1, dated Oct. 26, 2016.
Extended European Search Report for EPO Application No. 16174071.7, dated Oct. 19, 2016.
International Search Report for PCT/US2015/061108, dated May 26, 2016.
Notice of Allowance dated Dec. 5, 2016 for U.S. Appl. No. 13/975,162.
Office Action dated Dec. 19, 2016 for U.S. Appl. No. 14/753,402.
Office Action dated Jan. 18, 2017 for U.S. Appl. No. 14/475,736.
Notice of Allowance dated Feb. 16, 2017 for U.S. Appl. No. 14/943,772.
Notice of Allowance dated Apr. 4, 2017 for U.S. Appl. No. 14/548,793.
Office Action dated Apr. 4, 2017 for U.S. Appl. No. 14/753,402.
Examination Report for EP117514430, dated May 17, 2017.
Supplementary European Search Report for EP14863570, dated Jun. 30, 2017.
Supplementary European Search Report for EP14842625, dated Feb. 27, 2017.
Supplementary European Search Report for EP14864930, dated May 4, 2017.
Notice of Allowance dated Jul. 28, 2017 for U.S. Appl. No. 14/475,736; (pp. 1-8).
Office Action dated Aug. 21, 2017 for U.S. Appl. No. 14/753,402; (pp. 1-9).
Summary of Neurostimulation Systems Features, Advanced Neuromodulation Systems (ANS) home page, accessed on May 31, 2007 at http://web.archive.org/web/20040211224857/www.ans-nnedical.com/patients/WhichSystemIsBest/SumOfNeurostimulation.html.
EPO Search Report EP09704463, dated Jan. 10, 2011, Virender K. Sharma.
Ellis, et al., 'The Prevention of Experimentally Induced Reflux by Electrical Stimulation of the Distal Esophagus', American Journal of Surgery, vol. 115, Apr. 1968, 482-487.
Christensen et al., 'Physiologic Specialization at Esophagogastric Junction in Three Species' , American Journal of Physiology, vol. 225, No. 6, Dec. 1973, 1265-1270.
Gonzalez et al., 'Different Responsiveness of Excitatory and Inhibitory Enteric Motor Neurons in the Human Esophagus to Electrical Field Stimulation and to Nicotine' , Am J Physiol Gastrointest Liver Physiol, 287:G299-G306, 2004.
Kahrilas et al., 'Impact of Fundoplication on Bolus Transit Across Esophagogastric Junction' , American Physiological Society, 1998, 1386-1393.
Kamath et al., 'Neurocardiac and Cerebral Responses Evoked by Esophageal Vago-Afferent Stimulation in Humans: Effects of Varying Intensities' , Cardiovascular Research, 40 (1998) 591-599.
Lund et al., 'Electrical Stimulation of Esophageal Smooth Muscle and Effects of Antagonists' , American Journal of Physiology, vol. 217, No. 5, Nov. 1969, 1369-1374.
Stein et al., 'Three-dimensional Imaging of the Lower Esophageal Sphincter in Gastroesophageal Reflux Disease,' Annual Meeting of the American Surgical Association, Apr. 11-13, 1991, 374-383.
International Search Report for PCT/US2007/068907, dated Aug. 7, 2008.
International Search Report for PCT/US2008/056479, dated Aug. 20, 2008.
International Search Report for PCT/US2008/053780, dated Jun. 8, 2009.
International Search Report for PCT/US2011/027243, dated Jul. 8, 2011.
International Search Report for PCT/US2012/033695, dated Aug. 7, 2012.
International Search Report for PCT/US12/053576, dated Dec. 24, 2012.
International Search Report for PCT/US2012/036408, dated Aug. 17, 2012.

(56) References Cited

OTHER PUBLICATIONS

Clarke et al., 'An endoscopically implantable device stimulates the lower esophageal sphincter on demand by remote control: a study using a canine model', Endoscopy 2007; 39: 72-76.
International Search Report for PCT/US2013/056520, dated Apr. 4, 2014.
Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.
Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Cigaina, Valerio; Long-term Follow-Up of Gastric Stimulation for Obesity: The Mestre 8-Year Experience; Obesity Surgery; 14; 2004; S14-22.
Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Sanmiguel et al, 'Effect of electrical stimulation of the LES on LES pressure in a canine model'; Am J Physiol Gastrointest Live Physiol; 295: 389-394; 2008.
Clarke et al,. 'An Endoscopic Implantable Device Stimulates the LES On-Demand by Remote Control in a Canine Model'; Gastrointestinal Endoscopy, vol. 63, No. 5; 2006, AB103, 759.
Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.
Notice of Allowance dated Jul. 21, 2014 for U.S. Appl. No. 13/447,168.
Notice of Allowance dated Apr. 3, 2014 for U.S. Appl. No. 13/447,168.
Notice of Allowance dated Mar. 17, 2014 for U.S. Appl. No. 13/447,168.
Office Action dated Apr. 11, 2014 for U.S. Appl. No. 13/602,184.
Office Action dated Jul. 8, 2014 for U.S. Appl. No. 13/463,803.
Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.
Supplementary European Search Report for EP20120779639, Virender K. Sharma, dated Nov. 13, 2014.
European Search Opinion for EP20120779639, Virender K. Sharma, dated Nov. 25, 2014.
Notice of Allowance dated Dec. 24, 2014 for U.S. Appl. No. 13/463,803.
Notice of Allowance dated Jan. 20, 2015 for U.S. Appl. No. 13/602,184.
First Office Action for Application No. CN 01819456, dated Nov. 18, 2014.
Office Action dated Feb. 20, 2015 for U.S. Appl. No. 14/175,927.
Notice of Allowance dated Feb. 20, 2015 for U.S. Appl. No. 14/201,645.
Sallam et al, 'Feasibility of gastric electrical stimulation by percutaneous endoscopic transgastric electrodes'; Gastrointestinal Endoscopy; vol. 68, No. 4; 2008, 754-759.
Office Action dated Jun. 19, 2015 for U.S. Appl. No. 13/975,162.
Office Action dated Jun. 25, 2015 for U.S. Appl. No. 14/201,766.
Office Action dated Oct. 2, 2015 for U.S. Appl. No. 14/500,856.
Office Action dated Oct. 7, 2015 for U.S. Appl. No. 13/975,162.
International Search Report for PCT/US2014/053793, dated Mar. 27, 2015.
International Search Report for PCT/US2014/066565, dated Mar. 12, 2015.
International Search Report for PCT/US2014/066578, dated Mar. 19, 2015.
Jameison, GG et al. "Laparoscopic Nissen Fundoplication". Annals of Surgery, vol. 220. No. 2, p. 139 (1994).
Tam, Wce et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Notice of Allowance dated Jan. 20, 2016 for U.S. Appl. No. 14/201,766.
Examination Report for Australian Patent Application No. 2012242533, dated Oct. 5, 2015.
Office Action for Chinese Patent Application No. 201280028867.7, dated May 4, 2015.
Extended European Search Report for EPO Application No. 12771852.6, dated Aug. 28, 2014.
Examination Report for Australian Patent Application No. 2012250686, dated Nov. 4, 2015.
Examination Report for New Zealand Patent Application No. 616944, dated Jun. 17, 2014.
Examination Report for New Zealand Patent Application No. 616944, dated Nov. 2, 2015.
Office Action dated Feb. 1, 2016 for U.S. Appl. No. 14/475,736.
Second Office Action for Chinese Patent Application No. 201280028867.7, dated Mar. 21, 2016.
First Office Action for Chinese Patent Application No. 201380054290.1, dated Apr. 1, 2016.
Office Action dated Mar. 10, 2016 for U.S. Appl. No. 14/191,085.
Office Action dated Mar. 15, 2016 for U.S. Appl. No. 14/695,267.
Office Action dated Mar. 17, 2016 for U.S. Appl. No. 14/500,856.
Notice of Allowance dated Nov. 8, 2017 for U.S. Appl. No. 14/548,855; (pp. 1-8).
Office Action dated Dec. 20, 2017 for U.S. Appl. No. 14/753,402; (pp. 1-9).
Office Action dated Jan. 26, 2016 for U.S. Appl. No. 14/686,996.
Office Action dated Oct. 17, 2017 for U.S. Appl. No. 14/686,996; (pp. 1-13).
Office Action dated Dec. 21, 2017 for U.S. Appl. No. 15/594,903.
Examination Report for EP117514430, dated Jan. 17, 2018.

LAPAROSCOPIC LEAD FOR ESOPHAGEAL SPHINCTER IMPLANTATION

CROSS-REFERENCE

The present application is a divisional application of U.S. patent application Ser. No. 14/548,855 now U.S. Pat. No. 9,925,367, entitled "Laparoscopic Lead Implantation Method" filed on Nov. 20, 2014, which relies on U.S. Provisional Patent Application No. 61/906,825, entitled "Lead Implantation Method" and filed Nov. 20, 2013, for priority.

U.S. patent application Ser. No. 14/548,855 is also a continuation-in-part application of U.S. patent application Ser. No. 13/602,184, entitled "Endoscopic Lead Implantation Method", filed on Sep. 2, 2012, and issued as U.S. Pat. No. 9,037,245 on May 19, 2015, which relies on U.S. Provisional Patent Application No. 61/530,781, of the same title and filed on Sep. 2, 2011, for priority.

The present application is also related to U.S. patent application Ser. No. 14/191,085, entitled "Implantable Electrical Stimulation Leads", filed on Feb. 26, 2014, and issued as U.S. Pat. No. 9,498,619 on Nov. 22, 2016, which relies on U.S. Provisional Patent Application No. 61/769,732, of the same title and filed on Feb. 26, 2013, for priority.

All of the aforementioned applications are herein incorporated by reference in their entirety.

FIELD

The present specification relates generally to the electrical stimulation of biological tissues to provide therapy for physiological disorders. More particularly, the present specification relates to a method of laparoscopic implantation of electrically conductive leads proximate the lower esophageal sphincter (LES).

BACKGROUND

Electrical stimulation of nerves and surrounding tissue is used to treat a variety of conditions. For example, electrical stimulation can be used to restore partial function to limbs or organs following traumatic injury. Electrical stimulation can also be used to reduce pain. Specifically, electrical stimulation can be used to treat disorders associated with the gastrointestinal (GI) system, such as, obesity and gastroesophageal reflux disease (GERD).

Obesity is a common condition and a major public health problem in developed nations including the United States of America. As of 2009, more than two thirds of American adults, approximately 127 million people, were either overweight or obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States approximately $100 billion annually in direct and indirect health care expenses and in lost productivity. This trend is also apparent in many other developed countries.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m$^2$ is associated with significant co-morbidities. Morbid obesity is defined as possessing either a body weight more than 100 pounds greater than ideal or a body mass index (BMI) greater than 40 kg/m$^2$. Approximately 5% of the U.S. population meets at least one of the criteria for morbid obesity. Morbid obesity is associated with many diseases and disorders including, for example: diabetes; hypertension; heart attacks; strokes; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are also associated with morbid obesity. Taken together, the diseases associated with morbid obesity markedly reduce the odds of attaining an average lifespan. The sequelae raise annual mortality in affected people by a factor of 10 or more.

Gastro-esophageal reflux disease (GERD) is another common health problem and is expensive to manage in both primary and secondary care settings. This condition results from exposure of esophageal mucosa to gastric acid as the acid refluxes from the stomach into the esophagus. The acid damages the esophageal mucosa resulting in heartburn, ulcers, bleeding, and scarring, and long term complications such as Barrett's esophagus (pre-cancerous esophageal lining) and adeno-cancer of the esophagus.

Gastric electrical stimulation (GES) is aimed at treating both obesity and GERD. GES employs an implantable, pacemaker-like device to deliver low-level electrical stimulation to the gastrointestinal tract. For obesity, GES operates by disrupting the motility cycle and/or stimulating the enteric nervous system, thereby increasing the duration of satiety experienced by the patient. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Abiliti® implantable gastric stimulation device, manufactured by IntraPace, is currently available in Europe for treatment of obesity.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis, including nausea and vomiting.

Electrical stimulation has also been suggested for use in the treatment of GERD, wherein the stimulation is supplied to the lower esophageal sphincter (LES). For example, in U.S. Pat. No. 6,901,295, assigned to the applicant of the current invention, "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety.

Typically, the leads for LES stimulation are implanted in the lower esophageal wall using a laparoscopic approach. Lead implantation in the LES poses unique challenges different from implantation in any other part of the human body, including the stomach. One of the major challenges is the scarcity of space proximate the LES for the surgeon to maneuver. Another major challenge is exposure of the muscle tissue of the LES. The LES muscle tissue is covered by overlying fat tissue and the location of the gastroesophageal junction is difficult to identify. In addition, in a patient having a pre-existing gastrointestinal structural disorder, such as, a hiatal hernia, proper lead placement can be difficult to achieve. Often times the electrodes of the leads are not optimally positioned proximate the target tissue. Also, if a lead is not properly anchored, it can become dislodged and therapy will become ineffective. Therefore, what is needed is an effective and accurate method of implantation within the confined anatomy of the LES wherein the lead is securely fixed and/or anchored proximate the target tissue. What is also needed is an effective and accurate method of lead implantation that includes a hiatal closure as part of the implantation method.

SUMMARY

The present specification discloses a method of laparoscopically implanting at least one electrically conductive electrode, as part of an electrically conductive lead, proximate a lower esophageal sphincter (LES) of a patient, said method comprising the steps of: inserting the distal end of a laparoscope into an abdominal cavity of a patient through an incision in an abdominal wall of said patient; surgically exposing at least 2 cm of an anterior abdominal portion of a lower esophageal wall of said patient; delivering said electrically conductive electrode through a port on said laparoscope, wherein said lead comprises an elongate metal body having a proximal end and a distal end, said elongate body being covered in an electrically insulating material, said proximal end having a connector for connection to an implantable pulse generator and said distal end including said at least one exposed electrode and an anchoring member, said lead further comprising a first suture having a first end and a second end opposite said first end, wherein said first end is attached to a said distal end of said lead body and a first needle is attached to said second end; advancing said electrically conductive lead to a target position at an anterior surface of said exposed lower esophageal wall; using said first needle and said first suture to pass said electrode through said LES such that said exposed electrode comes to rest within or proximate a muscular layer of a wall of said LES and said first needle and a portion of said second end of said first suture re-emerge from said wall of said LES; applying at least one securing member to said portion of said second end of said suture at a distance at least 2-15 mm away from said wall of said LES; removing said first needle and excess first suture; and, fixing said anchoring member to proximate LES tissue by using a separate second needle to couple a second suture to said anchoring member.

The at least one securing member may comprise any one of a clip, suture, u-clip, or anchor.

Optionally, the at least one anchoring member comprises a butterfly tab having at least one opening and said step of coupling said second suture to said anchoring member comprises passing said second suture through said at least one opening. Optionally, the at least one anchoring member comprises a suture sleeve having at least one groove and said step of coupling said second suture to said anchoring member comprises passing said second suture around said at least one groove.

Optionally, the first suture comprises a barbed micro-architecture of a suture.

Optionally, the method further comprises the steps of repeating the steps of surgically exposing at least 2 cm of an anterior abdominal portion of a lower esophageal wall of said patient through fixing said anchoring member to proximate LES tissue by using a separate second needle to couple a second suture to said anchoring member to implant additional electrically stimulating leads.

The method further may comprise the step of using an external device to assess the impedance between each electrode to ensure accurate positioning of the electrodes within the muscularis layer of the lower esophageal wall.

The method further may comprise the step of endoscopically illuminating the lower esophageal sphincter to identify the appropriate location for dissection and placement of said at least one electrode.

The method may further comprise the step of endoscopically assessing lead placement to rule out perforation of said lower esophageal wall. The method may also further comprise the step of repositioning said lead if perforation of said lower esophageal wall has occurred.

Optionally, the implantation is combined with a hiatal hernia repair procedure to repair a hiatal hernia and prevent recurrence of a hiatal hernia in said patient.

The method may further comprise the steps of: exposing a diaphragmatic crura of said patient; and, applying at least one suture to said diaphragmatic crura.

The method may further comprise the step of attaching said proximal end of said lead to an implanted pulse generator.

The method may be used to implant a lead to treat esophageal disorders such as gastroesophageal reflux disease (GERD), achalasia, and esophageal dysmotility.

The present specification also discloses an electrically conductive lead for implanting proximate a lower esophageal sphincter of a patient, said lead comprising: an electrically conductive, elongate body having a proximal end and a distal end and covered in an insulating material; a connector at said proximal end for connecting to a pulse generator; at least one anchoring member positioned proximate said distal end of said lead body; at least one electrode positioned proximate said distal end of said lead body and distal to said at least one anchoring member; at least one length of suture having a first end and a second end opposite said first end, wherein said first end is attached to said distal end of said lead body; a needle attached to said second end of said at least one length of suture; and, at least one securing member removably applicable to said at least one length of suture.

Optionally, the elongate body comprises a straight metal wire. Optionally, the elongate body comprises a coiled metal wire. Optionally, the elongate body comprises a conducting cable.

The at least one securing member may comprise any one of a clip, suture, u-clip, or anchor.

Optionally, the at least one anchoring member comprises a butterfly tab having at least one opening. Optionally, the at least one anchoring member comprises a suture sleeve having at least one groove.

The present specification also discloses an electrically conductive lead for implanting proximate a lower esophageal sphincter of a patient, said lead comprising: an electrically conductive, elongate body having a proximal end and a distal end and covered in an insulating material; a connector at said proximal end for connecting to a pulse generator; a splitting element at said distal end for splitting said elongate body into two or more branches; two or more branches emanating from said splitting element, each branch having a proximal end and a distal end; at least one anchoring member positioned proximate said proximal end of each branch; at least one electrode positioned proximate said distal end of each branch; at least one length of suture having a first end and a second end opposite said first end, wherein said first end is attached to said distal end of each branch; a needle attached to said second end of said at least one length of suture; and, at least one securing member removably applicable to said at least one length of suture.

Optionally, the elongate body comprises a straight metal wire. Optionally, the elongate body comprises a coiled metal wire. Optionally, the elongate body comprises a conducting cable.

The at least one securing member may comprise any one of a clip, suture, u-clip, or anchor.

Optionally, the at least one anchoring member comprises a butterfly tab having at least one opening. Optionally, the at least one anchoring member comprises a suture sleeve having at least one groove.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
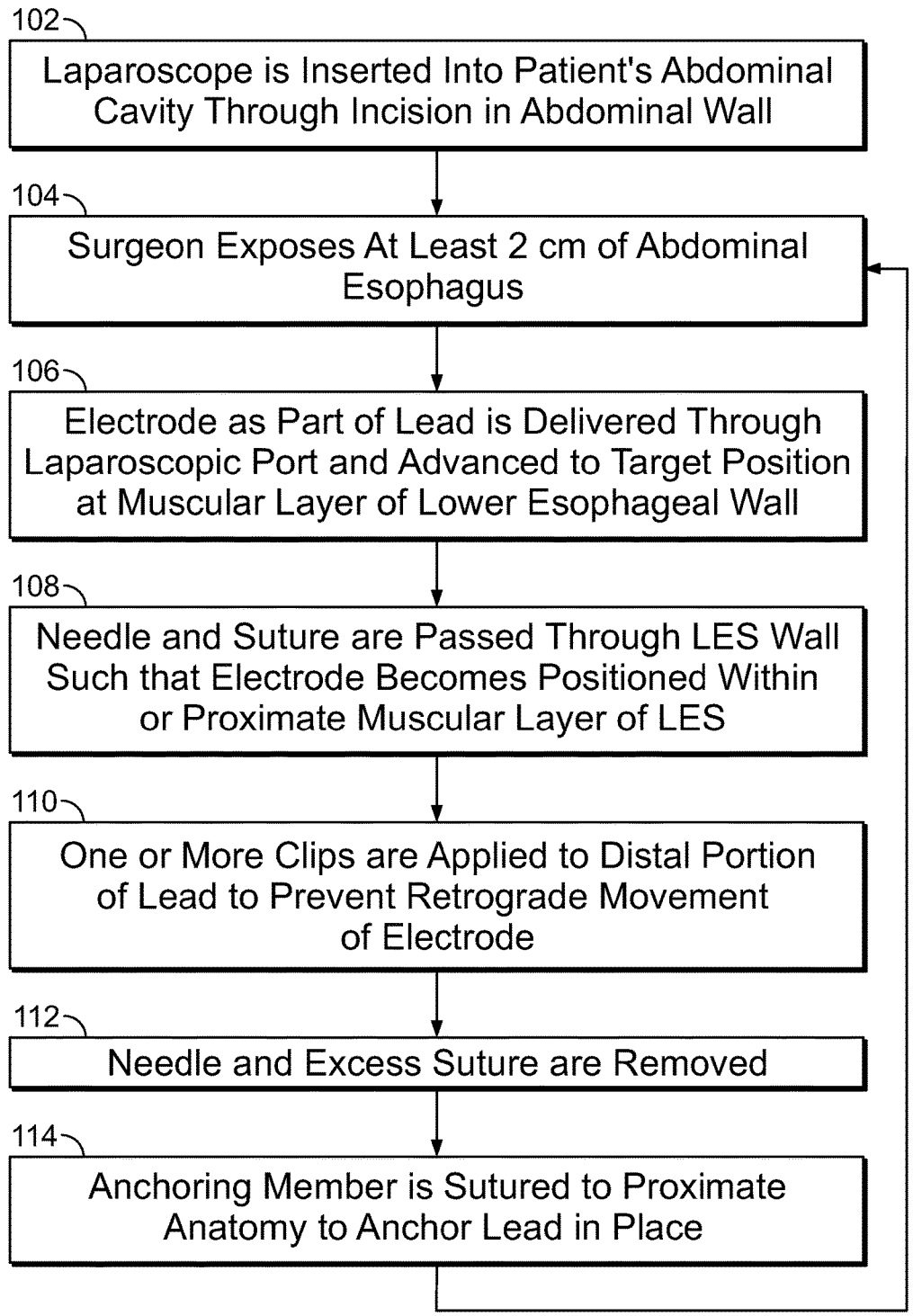
FIG. 1A is a flowchart illustrating the steps involved in one embodiment of a method of laparoscopically implanting at least one stimulating lead in the muscularis of a lower esophageal wall of a patient.

The present specification discloses a method of laparoscopically implanting one or more stimulating leads in the esophageal wall to be used with an electrical stimulation system directed toward treating at least one gastrointestinal disorder, such as gastroesophageal reflux disease (GERD). In various embodiments, the stimulating lead is defined as a lead having one or more stimulating electrodes. In one embodiment, the stimulating lead comprises an in-line lead having one stimulating electrode. In one embodiment, the stimulating lead comprises a bipolar lead having two stimulating electrodes. It should be appreciated that a stimulating lead having any number of stimulating electrodes can be used with the method of the present specification. The distal end of a laparoscope is inserted into the abdominal cavity of a patient through an incision in the patient's abdominal wall. A surgeon then exposes as least 2 cm of the abdominal esophagus. At least one stimulating lead is delivered through a laparoscopic port and the electrode(s) are advanced to a target position at the muscular portion of the esophageal wall. The lead comprises an elongate metal wire with an electrically insulating covering having a proximal end and a distal end. With respect to the lead, distal is used to describe the end that is positioned proximate the target tissue and proximal is used to describe the end that is connected to an implantable pulse generator (IPG), as described below.

In one embodiment, the elongate body comprises a straight metal wire. In another embodiment, the elongate body comprises a coiled metal wire. In yet another embodiment, the elongate body comprises a conducting cable. In one embodiment, the distal end of the lead comprises at least one branch or distal end wherein each branch or distal end includes an anchoring member and an exposed electrode. In various embodiments, the anchoring member comprises a butterfly tab with at least one opening. In one embodiment, each butterfly tab comprises two openings. In other embodiments, the anchoring mechanism comprises a suture sleeve with at least one groove. A length of non-absorbable suture (monofilament or multifilament) continues from the distal end of each branch or distal end of the lead and includes a stitching needle at its end opposite its attachment to the distal end of the branch. In one embodiment, the suture is comprised of nylon. In one embodiment, the suture comprises a barbed micro-architecture of a suture, such as the Covidien V-Lock™. The needle and suture are used to pass the exposed electrode into the muscularis of the LES. The electrode comes to rest within or proximate the muscularis of the LES. In various other embodiments, the electrode is positioned within or proximate the anterior gastric wall, gastric cardia or within 3 cm of the LES. For example, in one embodiment, the lead includes two electrodes wherein one is positioned within or proximate the anterior gastric wall and the other is positioned within or proximate the gastric cardia or the LES. The needle and suture re-emerge out of the LES wall. A portion of the lead proximate the distal end of the suture has at least one clip or securing member applied to it to prevent retrograde movement and/or dislodgement. In various embodiments, the clip is comprised of a metal. In one embodiment, the clip is titanium. In various embodiments, the clip is applied to the suture at least 2-15 mm away from the LES wall to allow for some slack between the clip and the LES. The clip acts as a distal stopper to prevent the electrode from sliding too far backwards and out of the LES muscular layer. The slack is provided to allow for gentle distension of surrounding GI tissues as a food bolus passes, thereby reducing the chances for tension or injury. The needle and excess suture are then removed. A separate needle with suture is used to stitch through the openings in the butterfly tab or around the grooves in the suture sleeve to hold the lead in place. During the application of these anchoring sutures to the butterfly tab or suture sleeve, the implanted electrode tends to move backwards, resulting in the first use of the clip in preventing backwards slippage of the electrode. The proximal end of the lead is then connected to an IPG that has been implanted in a subcutaneous pocket in the patient's abdomen.

In various embodiments, a length of up to 10 cm of suture remains distal to the clip. This provides several advantages. In the event that the clips are not tightly applied to the suture, they will tend to slide. It is preferable if the clips slide along the suture and not get lost in the abdominal cavity. A short suture end is stiff and traumatic to the surrounding organs, such as, the liver. A short suture end can easily puncture and damage surrounding tissues. In addition, a long suture is beneficial during removal of the lead. The long suture end acts as a locator of the distal end of the electrode and clip. Cutting the clip from the distal end of the suture is the first step in removing the electrode.

In one embodiment, a first stimulating lead is implanted with its electrodes positioned in the muscularis of the lower esophageal wall on the anterior surface of the esophagus. In various embodiments, additional stimulating leads are implanted into the muscularis of the lower esophageal wall in additional anatomical locations proximate the lower esophageal sphincter (LES).

In various embodiments, the method described above further includes using an external device to assess the impedance between each electrode implanted to ensure accurate positioning of the electrodes within the muscular layer of the target anatomy.

In many patients suffering from GERD, the anatomical area of the LES is "pushed up" or raised due to chronic esophagitis. In various embodiments, a light source is inserted endoscopically into these patients and the light is directed toward the anterior surface of the LES to assist with implantation by helping to direct the surgeon to the LES while minimizing the dissection.

In various embodiments, the method described above further includes endoscopically assessing lead placement to rule out perforation of the gastric wall or lower esophageal wall. If perforation is detected, the leads are withdrawn and repositioned.

In various embodiments, the method described above is used to implant leads in a patient having a hiatal hernia. The method further includes surgical dissection and exposure of the anatomy proximate the diaphragmatic crura. The surgeon surgically dissects the surrounding anatomy from the laparoscopic approach to implant the electrodes. In one embodiment, an area including at least 100 $mm^2$ of esophageal tissue proximate the LES is used for implantation. In various embodiments, the methods above are performed during a hiatal hernia repair to repair said hernia and prevent recurrence of a hiatal hernia as described with reference to co-pending U.S. patent application Ser. No. 13/975,162, filed Aug. 23, 2013 and entitled "Device and Implantation System for Electrical Stimulation of Biological Systems", which is hereby incorporated by reference in its entirety.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1A is a flowchart illustrating the steps involved in one embodiment of a method of laparoscopically implanting at least one stimulating lead in the muscularis of the lower esophageal wall of a patient. At step 102, a laparoscope is inserted with its distal end into a patient's abdominal cavity through an incision in the patient's abdominal wall. A surgeon exposes at least 2 cm of abdominal esophagus at step 104. An electrode, as part of a stimulating lead, is then delivered through a laparoscopic port and advanced to a target position at the muscular layer of the lower esophageal wall at step 106. Then, at step 108, a needle and suture attached to the distal end of the lead is used to pass through the LES wall and pull the electrode into the muscular layer of the LES. One or more clips are then applied to the suture of the lead at a position proximate the lead's distal end to prevent retrograde movement of the electrode at step 110. The needle and excess suture are removed at step 112. Then, at step 114, using a separate needle and suture, an anchoring member is sutured to the proximate anatomy to anchor the lead in place. In some embodiments, the anchoring member comprises a butterfly tab with at least one opening and the separate needle is used to pass the separate suture through the proximate anatomy and the at least one opening to secure the anchoring member in place. In other embodiments, the anchoring member comprises a suture sleeve with at least one groove and the separate needle is used to pass the separate suture through the proximate anatomy and around the groove to secure the anchoring member in place. Step 112 is typically performed prior to step 114 due to the traumatic nature of the needle. Optionally, in another embodiment, the original needle and suture are removed after securing the anchoring member. If additional leads are to be implanted, steps 104 through 114 are then repeated for each additional lead.

Figure 1B:
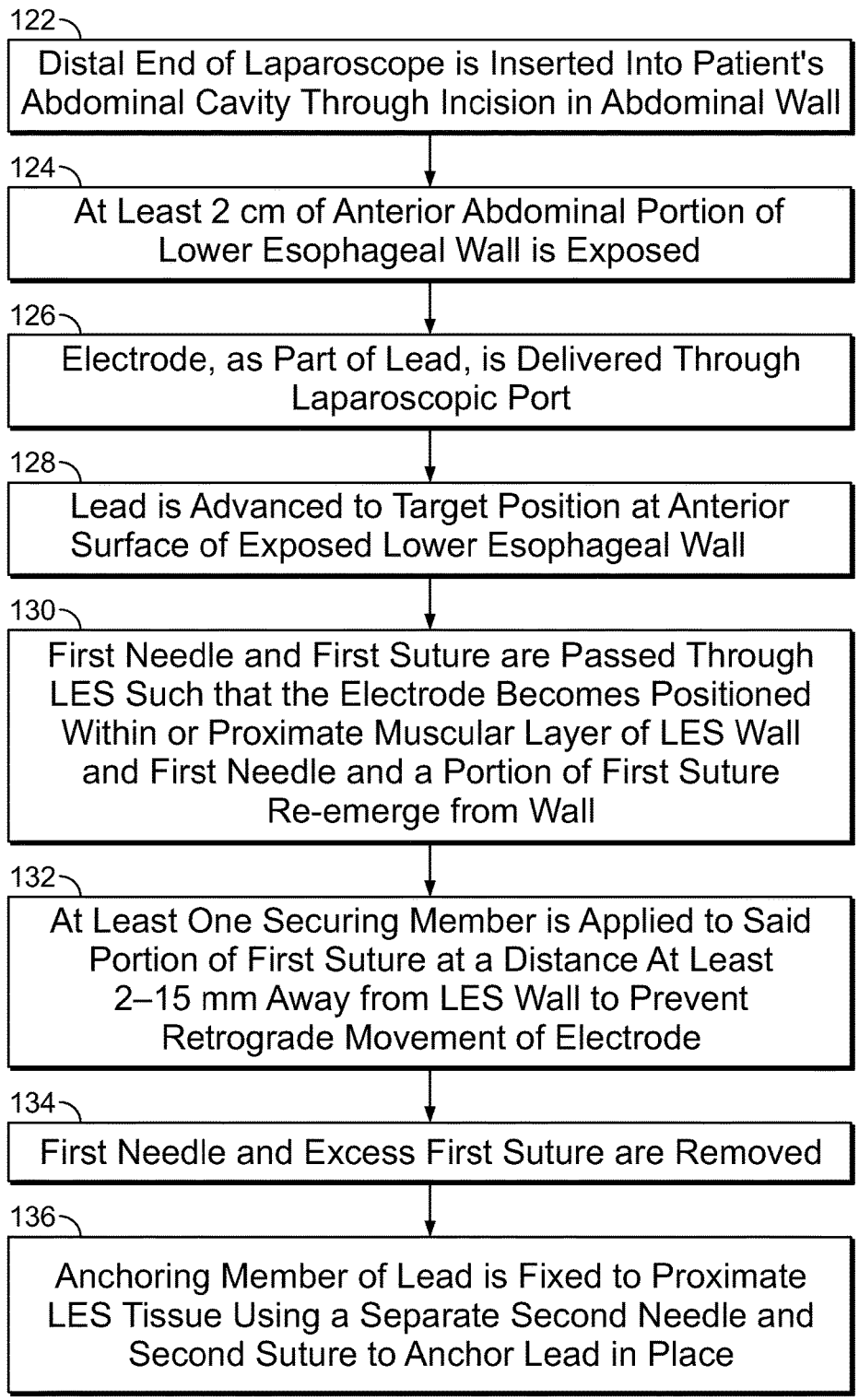
FIG. 1B is a flowchart illustrating the steps involved in another embodiment of a method of laparoscopically implanting at least one stimulating lead in the muscular layer of a lower esophageal wall of a patient.

FIG. 1B is a flowchart illustrating the steps involved in another embodiment of a method of laparoscopically implanting at least one stimulating lead in the muscular layer of a lower esophageal wall of a patient. At step 122, the distal end of a laparoscope is inserted into a patient's abdominal cavity through an incision in an abdominal wall of the patient. At least 2 cm of an anterior abdominal portion of a lower esophageal wall is then exposed at step 124. At least one electrode, as part of an electrically conducting lead, is delivered through a port on the laparoscope at step 126. At step 128, the lead is advanced to a target position at an anterior surface of the exposed lower esophageal wall. Then, at step 130, a first needle and first suture of the lead are passed through the LES such that the electrode becomes positioned within or proximate the muscular layer of the LES wall and the first needle and a portion of the first suture re-emerge from the wall. At least one securing member is then applied to the portion of the first suture at a distance at least 2-15 mm away from the LES wall to prevent retrograde movement of the electrode at step 132. The first needle and excess first suture are then removed at step 134. At step 136, an anchoring member on the lead is fixed to the proximate LES tissue using a separate second needle and second suture to anchor the lead in place.

Figure 2A:
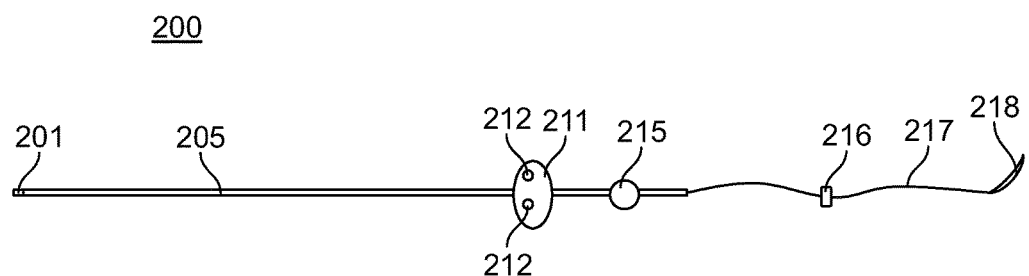
FIG. 2A is an illustration of an in-line electrically stimulating lead in accordance with one embodiment of the present specification.

FIG. 2A is an illustration of an in-line electrically stimulating lead 200 in accordance with one embodiment of the present specification. The lead 200 includes an elongate lead body 205 having a proximal end and a distal end. A connector 201 is positioned at the proximal end for connection to an implantable pulse generator. The distal end includes an anchoring member 211 and an electrode 215. Referring to FIG. 2A, the anchoring member 211 comprises a butterfly tab having two openings 212 for anchoring to body tissues after implantation. In other embodiments, the butterfly tab includes one or three or more openings. A suture 217 having a proximal end and a distal end is attached to the distal end of the lead body 205. A needle 218 is attached to the distal end of the suture 217. After implantation, at least one clip 216 is applied to the suture 217 emerging from the LES wall to prevent backward movement of the electrode 215.

Figure 2B:
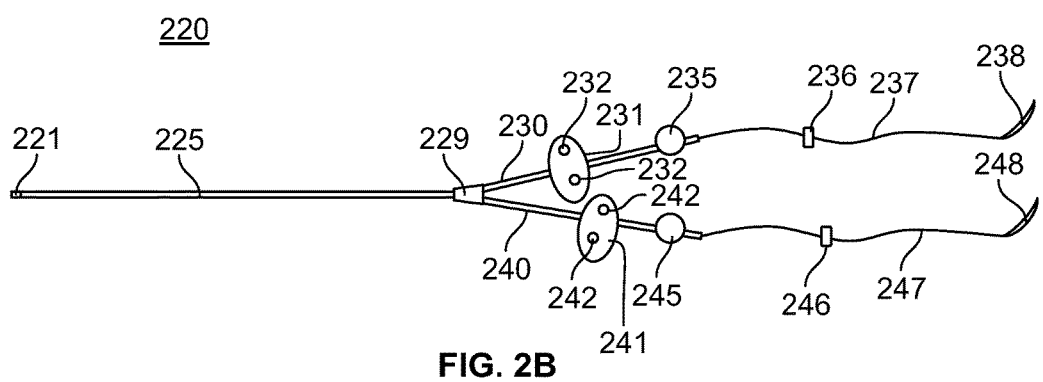
FIG. 2B is an illustration of bipolar electrically stimulating lead in accordance with one embodiment of the present specification.

FIG. 2B is an illustration of bipolar electrically stimulating lead 220 in accordance with one embodiment of the present specification. The lead 220 includes an elongate lead body 225 having a proximal end and a distal end. A connector 221 is positioned at the proximal end for connection to an implantable pulse generator. The distal end comprises a bifurcation point 229 that splits the lead body 225 into two branches or distal ends 230, 240. Each branch 230, 240 comprises an anchoring member 231, 241 and an electrode 235, 245. Referring to FIG. 2B, each anchoring member 231, 241 comprises a butterfly tab having two openings 232, 242 for anchoring to body tissues after implantation. In other embodiments, each butterfly tab includes one or three or more openings. A suture 237, 247 having a proximal end and a distal end is attached to the distal end of each branch 230, 240 of the lead 220. A needle 238, 248 is attached to the distal end of each suture 237, 247. After implantation, at least one clip 236, 246 is applied to each suture 237, 247 emerging from the LES wall to prevent backward movement of each electrode 235, 245.

Figure 2C:
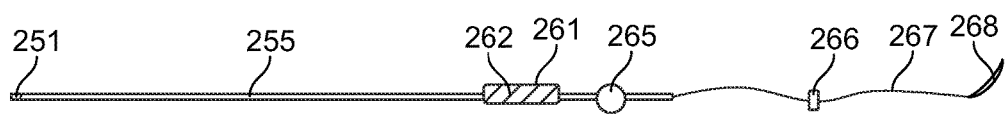
FIG. 2C is an illustration of an in-line electrically stimulating lead in accordance with another embodiment of the present specification.

FIG. 2C is an illustration of an in-line electrically stimulating lead 250 in accordance with another embodiment of the present specification. The lead 250 includes an elongate lead body 255 having a proximal end and a distal end. A connector 251 is positioned at the proximal end for connection to an implantable pulse generator. The distal end includes an anchoring member 261 and an electrode 265. Referring to FIG. 2C, the anchoring member 261 comprises a suture sleeve having a groove 262 for anchoring to body tissues after implantation. In other embodiments, the suture sleeve includes more than one groove. A suture 267 having a proximal end and a distal end is attached to the distal end of the lead body 255. A needle 268 is attached to the distal end of the suture 267. After implantation, at least one clip 266 is applied to the suture 267 emerging from the LES wall to prevent backward movement of the electrode 265.

Figure 2D:
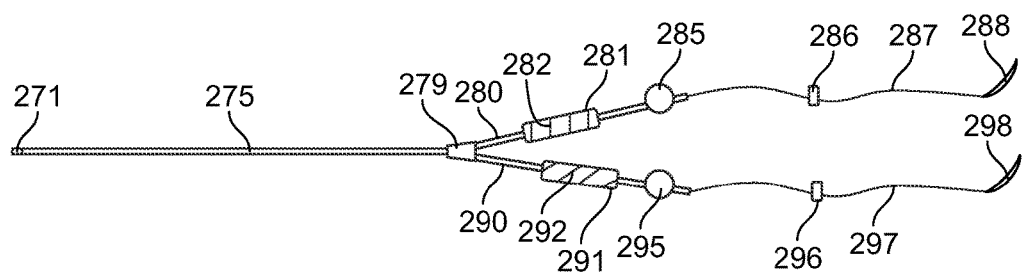
FIG. 2D is an illustration of bipolar electrically stimulating lead in accordance with another embodiment of the present specification.

FIG. 2D is an illustration of bipolar electrically stimulating lead 270 in accordance with another embodiment of the present specification. The lead 270 includes an elongate lead body 275 having a proximal end and a distal end. A connector 271 is positioned at the proximal end for connection to an implantable pulse generator. The distal end comprises a bifurcation point 279 that splits the lead body 275 into two branches or distal ends 280, 290. Each branch 280, 290 comprises an anchoring member 281, 291 and an electrode 285, 295. Referring to FIG. 2D, each anchoring member 281, 291 comprises a suture sleeve having a groove 282, 292 for anchoring to body tissues after implantation. In other embodiments, each suture sleeve includes more than one groove. A suture 287, 297 having a proximal end and a distal end is attached to the distal end of each branch 280, 290 of the lead 270. A needle 288, 298 is attached to the distal end of each suture 287, 297. After implantation, at least one clip 286, 296 is applied to each suture 287, 297 emerging from the LES wall to prevent backward movement of each electrode 285, 295.

Figure 3:
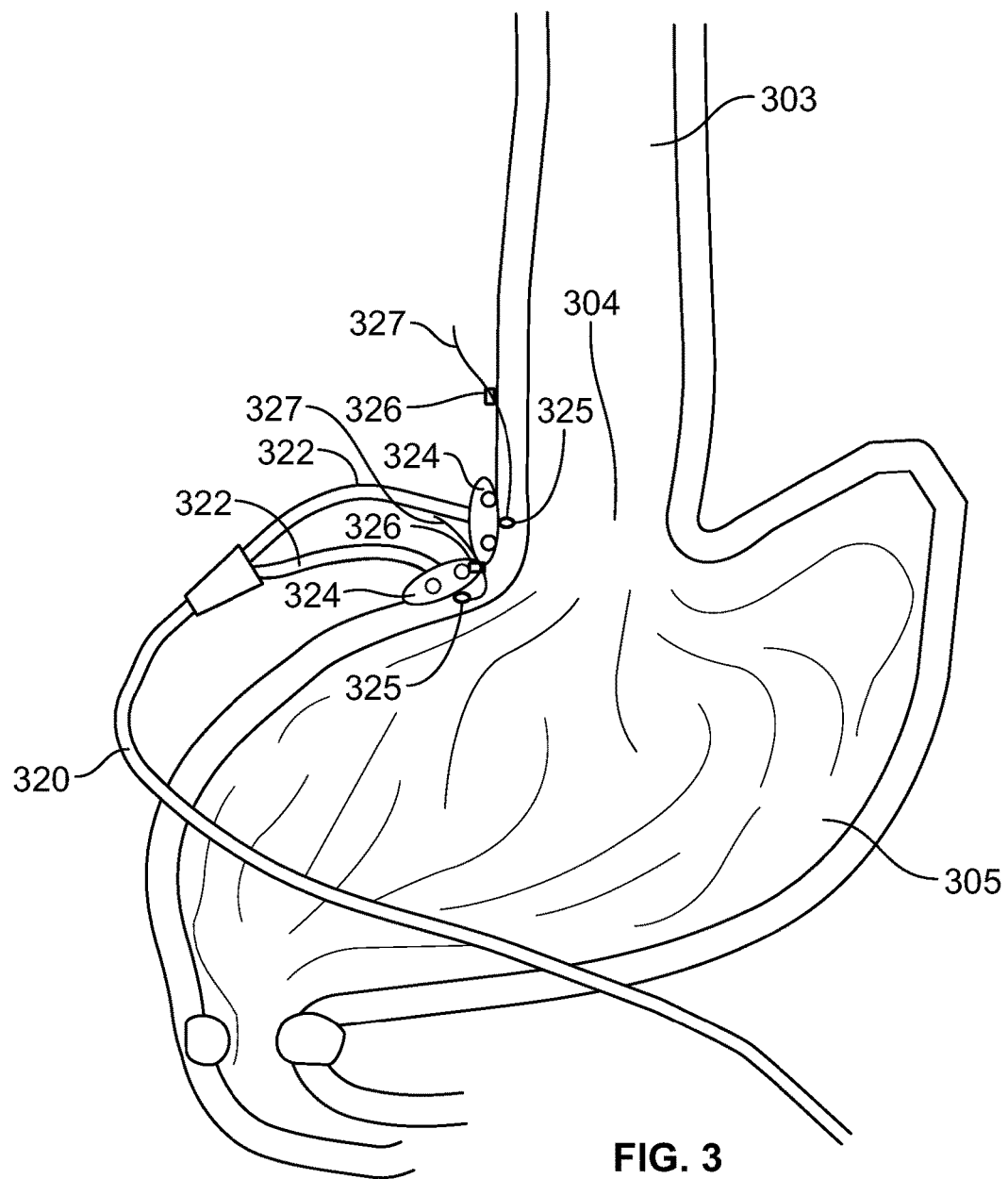
FIG. 3 is an illustration of the anatomical area proximate the lower esophageal sphincter (LES) of a patient depicting a single bipolar electrically stimulating lead that has been laparoscopically implanted using a method in accordance with one embodiment of the present specification.

FIG. 3 is an illustration of the anatomical area proximate the lower esophageal sphincter (LES) 304 of a patient depicting a single bipolar electrically stimulating lead 320 that has been laparoscopically implanted using a method in accordance with one embodiment of the present specification. The anatomical area of the LES 304 is depicted at the junction between the esophagus 303 and the stomach 305. Each lead 320 comprises two branches 322 wherein each branch 322 includes a butterfly tab 324 and an exposed electrode 325. The lead 320 has been implanted such that its electrodes 325 are positioned on a first side of the esophagus 303 within the muscular layer proximate the LES 304. Extending from the distal end of each branch 322 are the suture 327 and clip 326 preventing backward movement of the electrode 325.

Figure 4:
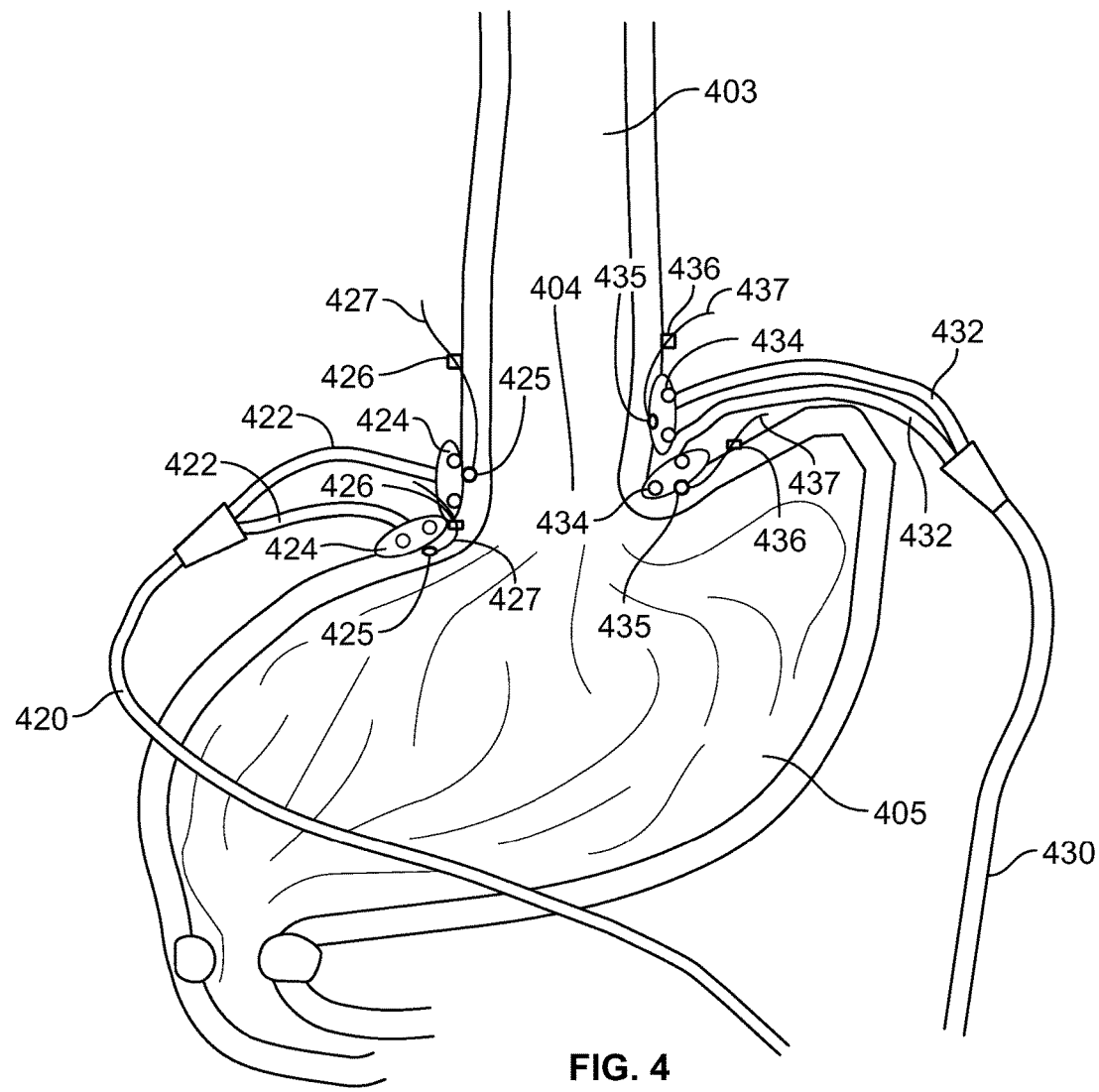
FIG. 4 is an illustration of the anatomical area proximate the lower esophageal sphincter (LES) of a patient depicting two bipolar electrically stimulating leads that have been laparoscopically implanted using a method in accordance with one embodiment of the present specification; and, FIG. 5 is a close up illustration of a distal end portion of an electrically stimulating lead depicting an electrode implanted within the muscular wall of the LES in accordance with one embodiment of the present specification.

FIG. 4 is an illustration of the anatomical area proximate the lower esophageal sphincter (LES) 404 of a patient depicting two bipolar electrically stimulating leads 420, 430 that have been laparoscopically implanted using a method in accordance with one embodiment of the present specification. The anatomical area of the LES 404 is depicted at the junction between the esophagus 403 and the stomach 405. Each lead 420, 430 comprises two branches 422, 432 wherein each branch 422, 432 includes a butterfly tab 424, 434 and an exposed electrode 425, 435. A first lead 420 has been implanted such that its electrodes 425 are positioned on a first side of the esophagus 403 within the muscular layer proximate the LES 404. A second lead 430 has been implanted such that its electrodes 435 are positioned on a second side of the esophagus 403, away and distinct from said first side, within the muscular layer proximate the LES 404. Extending from the distal end of each branch 422, 432 are the suture 427, 437 and clip 426, 436 preventing backward movement of the electrode 425, 435.

Figure 5:
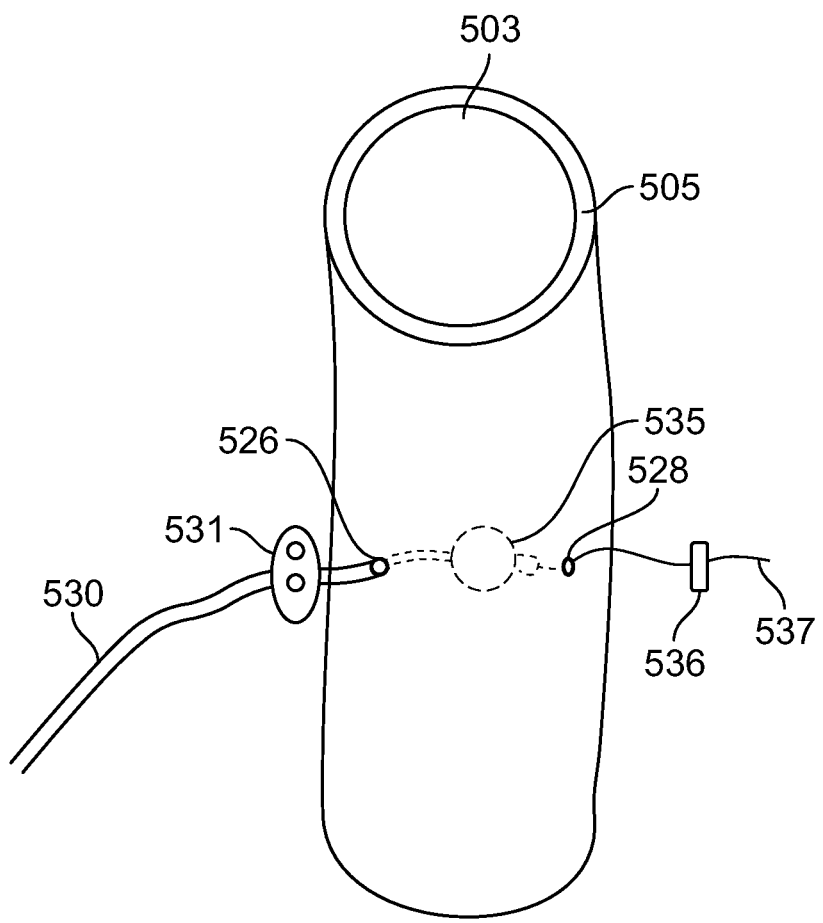

FIG. 5 is a close up illustration of a distal end portion 530 of an electrically stimulating lead depicting an electrode 535 implanted within the muscular wall 505 of the LES 503 in accordance with one embodiment of the present specification. The distal end portion 530 of the lead includes a butterfly tab 531 for anchoring to nearby anatomy. The butterfly tab 531 is depicted positioned proximal to an insertion point 526 of the distal end portion 530 of the lead into the wall of the LES 503. A suture 537 extends from the electrode 535 and emerges from the wall of the LES 503 at an exit point 528. The suture 537 includes a clip 536 applied to its distal end. The clip 537 cannot re-enter the wall of the LES 503 at the exit point 528 and thereby prevents backwards slippage of the electrode 535 out the insertion point 526. In one embodiment, anchoring of the distal end portion 530 of the lead with the butterfly tab 531 prevents slippage of the electrode 535 in the forward direction.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An electrically conductive lead for implanting proximate a lower esophageal sphincter of a patient, said lead comprising:
    an electrically conductive, elongate body having a proximal end and a distal end and covered in an insulating material;
    a connector at said proximal end for connecting to a pulse generator;
    at least one anchoring member positioned proximate said distal end of said lead body;
    at least one electrode positioned proximate said distal end of said lead body and distal to said at least one anchoring member;
    at least one length of suture having a first end and a second end opposite said first end, wherein said first end is attached to said distal end of said lead body;
    a needle attached to said second end of said at least one length of suture; and,
    at least one securing member removably applicable to said at least one length of suture.

2. The lead of claim 1, wherein said elongate body comprises a straight metal wire.

3. The lead of claim 1, wherein said elongate body comprises a coiled metal wire.

4. The lead of claim 1, wherein said elongate body comprises a conducting cable.

5. The lead of claim 1, wherein said at least one securing member comprises any one of a clip, suture, u-clip, or anchor.

6. The lead of claim 1, wherein said at least one anchoring member comprises a butterfly tab having at least one opening.

7. The lead of claim 1, wherein said at least one anchoring member comprises a suture sleeve having at least one groove.

8. An electrically conductive lead for implanting proximate a lower esophageal sphincter of a patient, said lead comprising:
    an electrically conductive, elongate body having a proximal end and a distal end and covered in an insulating material;
    a connector at said proximal end for connecting to a pulse generator;
    a splitting element at said distal end for splitting said elongate body into two or more branches;
    two or more branches emanating from said splitting element, each branch having a proximal end and a distal end;
    at least one anchoring member positioned proximate said proximal end of each branch;
    at least one electrode positioned proximate said distal end of each branch;
    at least one length of suture having a first end and a second end opposite said first end, wherein said first end is attached to said distal end of each branch;
    a needle attached to said second end of said at least one length of suture; and,
    at least one securing member removably applicable to said at least one length of suture.

9. The lead of claim 8, wherein said elongate body comprises a straight metal wire.

10. The lead of claim 8, wherein said elongate body comprises a coiled metal wire.

11. The lead of claim 8, wherein said elongate body comprises a conducting cable.

12. The lead of claim 8, wherein said at least one securing member comprises any one of a clip, suture, u-clip, or anchor.

13. The lead of claim 8, wherein said at least one anchoring member comprises a butterfly tab having at least one opening.

14. The lead of claim 8, wherein said at least one anchoring member comprises a suture sleeve having at least one groove.

* * * * *